US010369363B2

(12) United States Patent
Moffitt et al.

(10) Patent No.: US 10,369,363 B2
(45) Date of Patent: *Aug. 6, 2019

(54) ENHANCED DORSAL HORN STIMULATION USING MULTIPLE ELECTRICAL FIELDS

(71) Applicant: Boston Scientific Neuromodulation Corporation, Valencia, CA (US)

(72) Inventors: Michael A. Moffitt, Saugus, CA (US); Bradley Lawrence Hershey, Valencia, CA (US); Changfang Zhu, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/908,005

(22) Filed: Feb. 28, 2018

(65) Prior Publication Data
US 2018/0185646 A1    Jul. 5, 2018

Related U.S. Application Data

(63) Continuation of application No. 15/606,235, filed on May 26, 2017, now Pat. No. 9,925,380, which is a
(Continued)

(51) Int. Cl.
*A61N 1/05* (2006.01)
*A61N 1/36* (2006.01)

(52) U.S. Cl.
CPC ....... *A61N 1/36071* (2013.01); *A61N 1/0551* (2013.01); *A61N 1/36132* (2013.01); *A61N 1/36182* (2013.01); *A61N 1/36192* (2013.01)

(58) Field of Classification Search
CPC .. A61N 1/36071; A61N 1/361; A61N 1/0551; A61N 1/36132; A61N 1/36182; A61N 1/36185; A61N 1/36192
See application file for complete search history.

(56) References Cited

U.S. PATENT DOCUMENTS 6,516,227 B1   2/2003   Meadows et al.
6,675,046 B2   1/2004   Holsheimer
(Continued)

FOREIGN PATENT DOCUMENTS

AU   2015292709 B2   8/2018
CN   103796715 A    5/2014
(Continued)

OTHER PUBLICATIONS

"U.S. Appl. No. 14/805,741, Advisory Action dated Dec. 7, 2016", 3 pgs.
(Continued)

*Primary Examiner* — Paula J Stice
(74) *Attorney, Agent, or Firm* — Schwegman Lundberg & Woessner, P.A.

(57) ABSTRACT

A method of providing therapy to a patient having a medical condition comprises delivering electrical stimulation energy to the spinal cord of the patient in accordance with a stimulation program that preferentially stimulates dorsal horn neuronal elements over dorsal column neuronal elements in the spinal cord. The delivered electrical stimulation energy generates a plurality of electrical fields having different orientations that stimulate the dorsal horn neuronal elements.

20 Claims, 8 Drawing Sheets

Related U.S. Application Data continuation of application No. 14/805,741, filed on Jul. 22, 2015, now Pat. No. 9,662,495.

(60) Provisional application No. 62/028,643, filed on Jul. 24, 2014.

(56) References Cited

U.S. PATENT DOCUMENTS

| | | |
|---|---|---|
| 6,895,280 B2 | 5/2005 | Meadows et al. |
| 6,993,384 B2 | 1/2006 | Bradley et al. |
| 7,317,948 B1 | 1/2008 | King et al. |
| 7,333,857 B2 | 2/2008 | Campbell |
| 7,539,538 B2 | 5/2009 | Parramon et al. |
| 7,650,184 B2 | 1/2010 | Walter |
| 7,979,133 B2 | 7/2011 | Feler et al. |
| 8,019,439 B2 | 9/2011 | Kuzma et al. |
| 8,046,073 B1 | 10/2011 | Pianca |
| 8,224,453 B2 | 7/2012 | De Ridder |
| 8,255,057 B2 | 8/2012 | Fang et al. |
| 8,355,797 B2 | 1/2013 | Caparso et al. |
| 8,380,318 B2 | 2/2013 | Kishawi et al. |
| 8,455,716 B2 | 6/2013 | Huang et al. |
| 8,504,147 B2 | 8/2013 | Deem et al. |
| 8,615,300 B2 | 12/2013 | Feler et al. |
| 8,649,874 B2 | 2/2014 | Alataris et al. |
| 8,670,831 B2 | 3/2014 | Wacnik et al. |
| 8,676,329 B2 | 3/2014 | Wacnik et al. |
| 8,676,331 B2 | 3/2014 | Parker |
| 8,731,675 B2 | 5/2014 | Ranu et al. |
| 9,597,517 B2 | 3/2017 | Moffitt |
| 9,662,495 B2 | 5/2017 | Moffitt et al. |
| 9,925,380 B2 | 3/2018 | Moffitt et al. |
| 2003/0139781 A1 | 7/2003 | Bradley et al. |
| 2004/0167584 A1 | 8/2004 | Carroll et al. |
| 2005/0055065 A1 | 3/2005 | Campbell |
| 2006/0253182 A1 | 11/2006 | King |
| 2007/0150036 A1 | 6/2007 | Anderson |
| 2007/0168008 A1 | 7/2007 | Olsen |
| 2008/0188909 A1 | 8/2008 | Bradley |
| 2009/0054936 A1* | 2/2009 | Eggen .................. A61N 1/05 607/2 |
| 2009/0204173 A1 | 8/2009 | Fang et al. |
| 2009/0281596 A1 | 11/2009 | King et al. |
| 2010/0010566 A1 | 1/2010 | Thacker et al. |
| 2010/0030298 A1 | 2/2010 | Martens et al. |
| 2010/0121409 A1 | 5/2010 | Kothandaraman et al. |
| 2010/0137943 A1 | 6/2010 | Zhu |
| 2010/0249875 A1 | 9/2010 | Kishawi et al. |
| 2010/0274312 A1 | 10/2010 | Alataris et al. |
| 2010/0274314 A1 | 10/2010 | Alataris et al. |
| 2010/0274315 A1 | 10/2010 | Alataris et al. |
| 2010/0274317 A1 | 10/2010 | Parker et al. |
| 2010/0274318 A1 | 10/2010 | Walker et al. |
| 2010/0274326 A1 | 10/2010 | Chitre et al. |
| 2011/0009923 A1 | 1/2011 | Lee |
| 2011/0040348 A1 | 2/2011 | Wacnik et al. |
| 2011/0184486 A1 | 7/2011 | De Ridder |
| 2012/0059446 A1 | 3/2012 | Wallace et al. |
| 2012/0083709 A1 | 4/2012 | Parker et al. |
| 2012/0172946 A1 | 7/2012 | Konstantinos et al. |
| 2012/0253422 A1 | 10/2012 | Thacker et al. |
| 2012/0265279 A1 | 10/2012 | Zhu et al. |
| 2012/0283797 A1 | 11/2012 | De Ridder |
| 2012/0290041 A1 | 11/2012 | Kim et al. |
| 2013/0066411 A1 | 3/2013 | Thacker et al. |
| 2013/0116752 A1 | 5/2013 | Parker et al. |
| 2013/0253611 A1* | 9/2013 | Lee .................. A61N 1/36185 607/59 |
| 2013/0268021 A1 | 10/2013 | Moffitt |
| 2013/0296975 A1 | 11/2013 | Lee et al. |
| 2014/0058481 A1 | 2/2014 | Perryman et al. |
| 2014/0081349 A1 | 3/2014 | Lee et al. |
| 2014/0277267 A1 | 9/2014 | Vansickle et al. |
| 2015/0032022 A1 | 1/2015 | Stone et al. |
| 2015/0151125 A1 | 6/2015 | Zhu et al. |
| 2016/0022994 A1 | 1/2016 | Moffitt et al. |
| 2017/0259062 A1 | 9/2017 | Moffitt et al. |

FOREIGN PATENT DOCUMENTS

| | | |
|---|---|---|
| CN | 106659885 A | 5/2017 |
| JP | 2017523835 A | 8/2017 |
| WO | WO-2006029257 A2 | 3/2006 |
| WO | WO-2006135791 A2 | 12/2006 |
| WO | WO-2013067018 A3 | 8/2013 |
| WO | WO-2016014624 | 1/2016 |

OTHER PUBLICATIONS

"U.S. Appl. No. 14/805,741, Examiner Interview Summary dated Dec. 29, 2016", 3 pgs.

"U.S. Appl. No. 14/805,741, Final Office Action dated Sep. 9, 2016", 11 pgs.

"U.S. Appl. No. 14/805,741, Non Final Office Action dated Apr. 21, 2016", 11 pgs.

"U.S. Appl. No. 14/805,741, Notice of Allowance dated Feb. 1, 2017", 9 pgs.

"U.S. Appl. No. 14/805,741, Response filed Jan. 9, 2017 to Advisory Action dateded Dec. 7, 2016", 10 pgs.

"U.S. Appl. No. 14/805,741, Response filed Jul. 20, 2016 to Non Final Office Action dated Apr. 21, 2016", 9 pgs.

"U.S. Appl. No. 14/805,741, Response filed Nov. 7, 2016 to Final Office Action dated Sep. 9, 2016", 9 pgs.

"U.S. Appl. No. 15/606,235, Non Final Office Action dated Jul. 28, 2017", 12 pgs.

"U.S. Appl. No. 15/606,235, Notice of Allowance dated Nov. 14, 2017", 7 pgs.

"U.S. Appl. No. 15/606,235, Response filed Oct. 24, 2017 to Non Final Office Action dated Jul. 28, 2017", 9.

"Australian Application Serial No. 2015292709, First Examiners Report dated Sep. 8, 2017", 3 pgs.

"European Application Serial No. 15744453.0, Response filed Sep. 13, 2017 to Communication Pursuant to Rules 161(1) and 162 EPC dated Mar. 8, 2017", 11 pgs.

"International Application Serial No. PCT/US2015/041469, International Preliminary Report on Patentability dated Feb. 2, 2017", 8 pgs.

"International Application Serial No. PCT/US2015/041469, International Search Report dated Nov. 3, 2015", 5 pgs.

"International Application Serial No. PCT/US2015/041469, Written Opinion dated Nov. 3, 2015", 6 pgs.

Barker, John Michael, "Temporary Neurostimulation Lead Identification Device", U.S. Appl. No. 61/030,506, filed Feb. 21, 2008.

Rao, Prakash, et al., "Technique for Linking Electrodes Together During Programming of Neurostimulation System", U.S. Appl. No. 61/561,760, filed Nov. 18, 2011.

Vansickle, Dennis Allen, "Systems and Methods for Delivering Sub-Threshold Therapy to a Patient", U.S. Appl. No. 61/801,917, filed Mar. 15, 2013.

"Australian Application Serial No. 2015292709, Response filed Mar. 27, 2018 to First Examiners Report dated Sep. 8, 2017", 12 pgs.

"Canadian Application Serial No. 2,954,855, Office Action dated Aug. 31, 2018", 4 pgs.

"Canadian Application Serial No, 2,954,855, Response filed Apr. 27, 2018 to Office Action dated Oct. 30, 2017", 22 pgs.

"Chinese Application Serial No. 201580040319.X, Office Action dated Jul. 31, 2018", w/ English translation, 24 pgs.

"European Application Serial No. 15744453.0, Communication Pursuant o Article 94(3) EPC dated Oct. 8, 2018", 6 pgs.

"Japanese Application Serial No. 2017-504083, Examiners Decision of Final Refusal dated Sep. 25, 2018", W/English Translation, 6 pgs.

(56) References Cited

OTHER PUBLICATIONS

"Japanese Application Serial No. 2017-504083, Response filed Apr. 11, 2018 to Office Action dated Jan. 11, 2018", w/ English claims, 31 pgs.

* cited by examiner

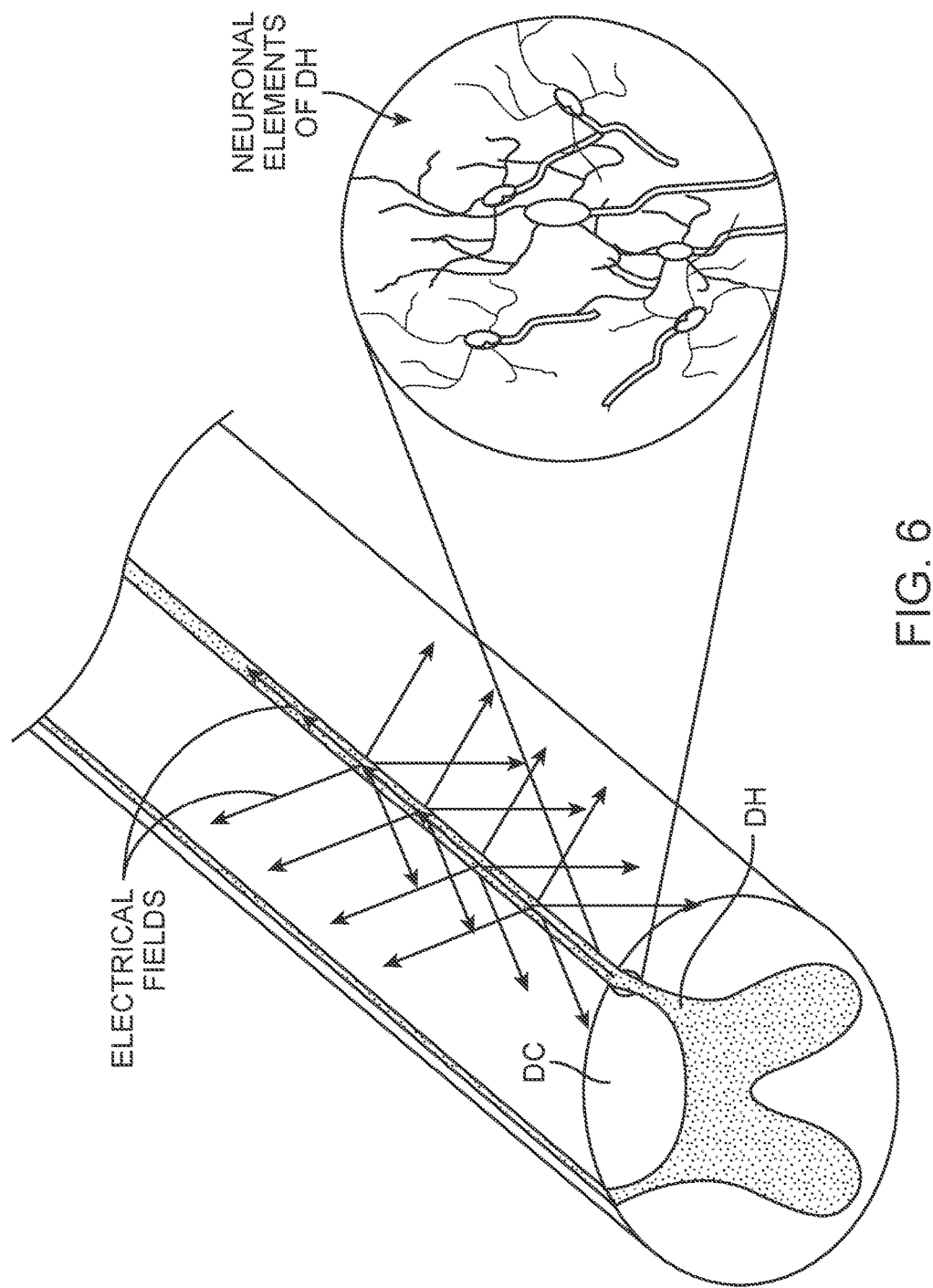

ENHANCED DORSAL HORN STIMULATION USING MULTIPLE ELECTRICAL FIELDS

CLAIM OF PRIORITY

This application is a continuation of U.S. application Ser. No. 15/606,235, filed May 26, 2017, which is a continuation of U.S. application Ser. No. 14/805,741, filed Jul. 22, 2015, now issued as U.S. Pat. No. 9,662,495, which claims the benefit of priority under 35 U.S.C. § 119(e) of U.S. Provisional Patent Application Ser. No. 62/028,643, filed on Jul. 24, 2014, each of which is herein incorporated by reference in its entirety.

FIELD OF THE INVENTION

The present invention relates to implantable medical systems, and more particularly, to systems and methods for stimulating tissue.

BACKGROUND OF THE INVENTION

Implantable neurostimulation systems have proven therapeutic in a wide variety of diseases and disorders. For example, Spinal Cord Stimulation (SCS) techniques, which directly stimulate the spinal cord tissue of the patient, have long been accepted as a therapeutic modality for the treatment of chronic neuropathic pain syndromes, and the application of spinal cord stimulation has expanded to include additional applications, such as angina pectoralis, peripheral vascular disease, and incontinence, among others. Spinal cord stimulation is also a promising option for patients suffering from motor disorders, such as Parkinson's Disease, Dystonia and essential tremor.

SCS systems typically include one or more electrode carrying stimulation leads, which are implanted at the desired stimulation site, and a neurostimulator (e.g., an implantable pulse generator (IPG)) implanted remotely from the stimulation site, but coupled either directly to the neurostimulation lead(s) or indirectly to the neurostimulation lead(s) via a lead extension.

Electrical stimulation energy may be delivered from the IPG to the electrodes in the form of an electrical pulsed waveform. Thus, electrical pulses can be delivered from the IPG to the neurostimulation leads to stimulate the spinal cord tissue and provide the desired efficacious therapy to the patient. The configuration of electrodes used to deliver electrical pulses to the targeted spinal cord tissue constitutes an electrode configuration, with the electrodes capable of being selectively programmed to act as anodes (positive), cathodes (negative), or left off (zero). In other words, an electrode configuration represents the polarity being positive, negative, or zero. Other parameters that may be controlled or varied include the amplitude, pulse width, and rate (or frequency) of the electrical pulses provided through the electrode array. Each electrode configuration, along with the electrical pulse parameters, can be referred to as a "stimulation parameter set."

The SCS system may further comprise a handheld patient programmer in the form of a remote control (RC) to remotely instruct the IPG to generate electrical stimulation pulses in accordance with selected stimulation parameters. Typically, the stimulation parameters programmed into the IPG can be adjusted by manipulating controls on the RC to modify the electrical stimulation provided by the IPG system to the patient. Thus, in accordance with the stimulation parameters programmed by the RC, electrical pulses can be delivered from the IPG to the stimulation electrode(s) to stimulate or activate a volume of tissue in accordance with a set of stimulation parameters and provide the desired efficacious therapy to the patient. The best stimulus parameter set will typically be one that delivers stimulation energy to the volume of tissue that must be stimulated in order to provide the therapeutic benefit (e.g., treatment of pain), while minimizing the volume of non-target tissue that is stimulated.

However, the number of electrodes available combined with the ability to generate a variety of complex electrical pulses, presents a huge selection of stimulation parameter sets to the clinician or patient. For example, if the SCS system to be programmed has an array of sixteen electrodes, millions of stimulation parameter sets may be available for programming into the SCS system. Today, SCS systems may have up to thirty-two electrodes, thereby exponentially increasing the number of stimulation parameters sets available for programming.

To facilitate such selection, the clinician generally programs the IPG through a computerized programming system; for example, a clinician's programmer (CP). The CP can be a self-contained hardware/software system, or can be defined predominantly by software running on a standard personal computer (PC). The CP may actively control the characteristics of the electrical stimulation generated by the IPG to allow the optimum stimulation parameters to be determined based on patient feedback or other means and to subsequently program the IPG with the optimum stimulation parameter sets.

For example, in order to achieve an effective result from conventional SCS, the lead or leads must be placed in a location, such that the electrical stimulation energy creates a sensation known as paresthesia, which can be characterized as an alternative sensation that replaces the pain signals sensed by the patient. The paresthesia induced by the stimulation and perceived by the patient should be located in approximately the same place in the patient's body as the pain that is the target of treatment. If a lead is not correctly positioned, it is possible that the patient will receive little or no benefit from an implanted SCS system. Thus, correct lead placement can mean the difference between effective and ineffective pain therapy. When leads are implanted within the patient, the CP, in the context of an operating room (OR) mapping procedure, may be used to instruct the IPG to apply electrical stimulation to test placement of the leads and/or electrodes, thereby assuring that the leads and/or electrodes are implanted in effective locations within the patient.

Once the leads are correctly positioned, a fitting procedure, which may be referred to as a navigation session, may be performed using the CP to program the RC, and if applicable the IPG, with a set of stimulation parameters that best addresses the painful site. Thus, the navigation session may be used to pinpoint the VOA or areas correlating to the pain. Such programming ability is particularly advantageous for targeting the tissue during implantation, or after implantation should the leads gradually or unexpectedly move that would otherwise relocate the stimulation energy away from the target site. By reprogramming the IPG (typically by independently varying the stimulation energy on the electrodes), the VOA can often be moved back to the effective pain site without having to re-operate on the patient in order to reposition the lead and its electrode array. When adjusting the VOA relative to the tissue, it is desirable to make small changes in the proportions of current, so that changes in the spatial recruitment of nerve fibers will be perceived by the patient as being smooth and continuous and to have incremental targeting capability.

Conventional SCS programming has as its therapeutic goal maximal stimulation (i.e., recruitment) of dorsal column (DC) nerve fibers that run in the white matter along the longitudinal axis of the spinal cord and minimal stimulation of other fibers that run perpendicular to the longitudinal axis of the spinal cord (dorsal root (DR) nerve fibers, predominantly), as illustrated in FIG. 1. The white matter of the dorsal column includes mostly large myelinated axons that form afferent fibers. Thus, conventionally, the large sensory afferents of the DC nerve fibers have been targeted for stimulation at an amplitude that provides pain relief.

While the full mechanisms are pain relief are not well understood, it is believed that the perception of pain signals is inhibited via the gate control theory of pain, which suggests that enhanced activity of innocuous touch or pressure afferents via electrical stimulation creates interneuronal activity within the dorsal horn (DH) of the spinal cord that releases inhibitory neurotransmitters (Gamma-Aminobutyric Acid (GABA), glycine), which in turn, reduces the hypersensitivity of wide dynamic range (WDR) sensory neurons to noxious afferent input of pain signals traveling from the dorsal root (DR) neural fibers that innervate the pain region of the patient, as well as treating general WDR ectopy. Consequently, stimulation electrodes are typically implanted within the dorsal epidural space to provide stimulation to the DC nerve fibers.

As illustrated in FIG. 1, the DH can be characterized as central "butterfly" shaped central area of gray matter (neuronal cell bodies) substantially surrounded by an ellipse-shaped outer area of white matter (myelinated axons). The DH is the dorsal portion of the "butterfly" shaped central area of gray matter, which includes neuronal cell terminals, neuronal cell bodies, dendrites, and axons.

Activation of large sensory fibers also typically creates the paresthesia sensation that often accompanies SCS therapy. Although alternative or artifactual sensations, such as paresthesia, are usually tolerated relative to the sensation of pain, patients sometimes report these sensations to be uncomfortable, and therefore, they can be considered an adverse side-effect to neuromodulation therapy in some cases.

It has been shown that the neuronal elements (e.g., neurons, dendrites, axons, cell bodies, and neuronal cell terminals) in the DH can be preferentially stimulated over the DC neuronal elements by minimizing the longitudinal gradient of an electrical field generated by a neurostimulation lead along the DC, thereby providing therapy in the form of pain relief without creating the sensation of paresthesia. Such a technique is described in U.S. Provisional Patent Application Ser. No. 61/911,728, entitled "Systems and Methods for Delivering Therapy to the Dorsal Horn of a Patient," which is expressly incorporated herein by reference.

This technique relies, at least partially on the natural phenomenon that DH fibers and DC fibers have different responses to electrical stimulation. The strength of stimulation (i.e., depolarizing or hyperpolarizing) of the DC fibers and neurons is described by the so-called "activating function" $\partial^2 V/\partial x^2$ which is proportional to the second-order spatial derivative of the voltage along the longitudinal axis of the spine. This is partially because the large myelinated axons in DC are primarily aligned longitudinally along the spine. On the other hand, the likelihood of generating action potentials in DH fibers and neurons is described by the "activating function" $\partial V/\partial x$ (otherwise known as the electric field). The DH "activating function" is proportional not to the second-order derivative, but to the first-order derivative of the voltage along the fiber axis. Accordingly, distance from the electrical field locus affects the DH "activating function" less than it affects the DC "activating function."

While fibers in the DC run in an axial direction, the neuronal elements in the dorsal horn are oriented in many directions, including perpendicular to the longitudinal axis of the spinal cord. However, as illustrated in FIG. 2, the dorsal horn stimulation technique described in U.S. Provisional Patent Application Ser. No. 61/911,728, generates an electrical field that is uniformly in one direction. There, thus, remains a need for an improved technique to stimulate the neuronal elements of the dorsal horn.

SUMMARY OF THE INVENTION

In accordance with the present inventions, a method of providing therapy to a patient having a medical condition (e.g., chronic pain) is provided. The method comprises delivering electrical stimulation energy (e.g., anodic) to the spinal cord of the patient in accordance with a stimulation program that preferentially stimulates dorsal horn neuronal elements over dorsal column neuronal elements in the spinal cord. In one method, the electrical stimulation energy is delivered to the spinal cord of the patient without creating the sensation of paresthesia in the patient. The delivered electrical stimulation energy generates a plurality of electrical fields having different orientations that stimulate the dorsal horn neuronal elements. For example, the plurality of electrical fields may be orientated in different medio-lateral directions or different rostro-caudal directions.

In one method, the electrical stimulation energy is delivered to the spinal cord of the patient as a pulsed electrical waveform, in which case, the plurality of electrical fields may be respectively generated on a pulse-by-pulse basis. In another method, the plurality of electrical fields achieve temporal summation of stimulation in the dorsal horn neuronal elements. In still another method, the electrical stimulation energy is delivered from an electrical stimulation lead implanted along a longitudinal axis of the spinal cord of the patient. The electrical stimulation lead may carry a plurality of electrodes, in which case, all of the electrodes may be activated to generate each electrical field.

An optional method further comprises cycling through the electrical fields multiple times. The electrical fields may, e.g., be generated the same number of times for each electrical field cycle, generated a different number of times for each electrical field cycle, generated in the same order during the electrical field cycles, generated in a different order during the electrical field cycles, or bursted on and off at a burst frequency. In the latter case, the burst frequency may match a pathological burst frequency of medical condition.

In one method, the electrical stimulation energy may be delivered from a plurality of electrodes implanted adjacent the spinal cord of the patient. In this case, the electrodes may be radially segmented electrodes. This method may further comprise determining a stimulation threshold for each of the electrodes, and generating each of the electrical fields based on the stimulation thresholds of the electrodes. In this case, determining the stimulation threshold for each of the electrodes may comprise automatically delivering electrical energy from each of the electrodes at different amplitudes, automatically measuring an evoked compound action potential in response to the deliverance of the electrical energy from each of the electrodes, and automatically recording the amplitude at which the evoked compound action potential is measured for each of the electrodes. Or, determining the stimulation threshold for each of the electrodes may comprise automatically delivering electrical energy from each of the electrodes at different amplitudes, acquiring feedback from the patient in response to the deliverance of the electrical energy from each of the electrodes, and automatically recording the amplitude at which paresthesia is perceived by the patient for each of the electrodes.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 3 is a plan view of the SCS system of FIG. 1 in use to perform deep brain stimulation (DBS) on a patient;

FIG. 6 is a perspective view of the spinal cord of a patient, wherein the SCS system of FIG. 2 is used to generate multiple electrical fields that stimulate the neuronal elements of the dorsal horn of the spinal cord;

DETAILED DESCRIPTION OF THE EMBODIMENTS

Figure 1:
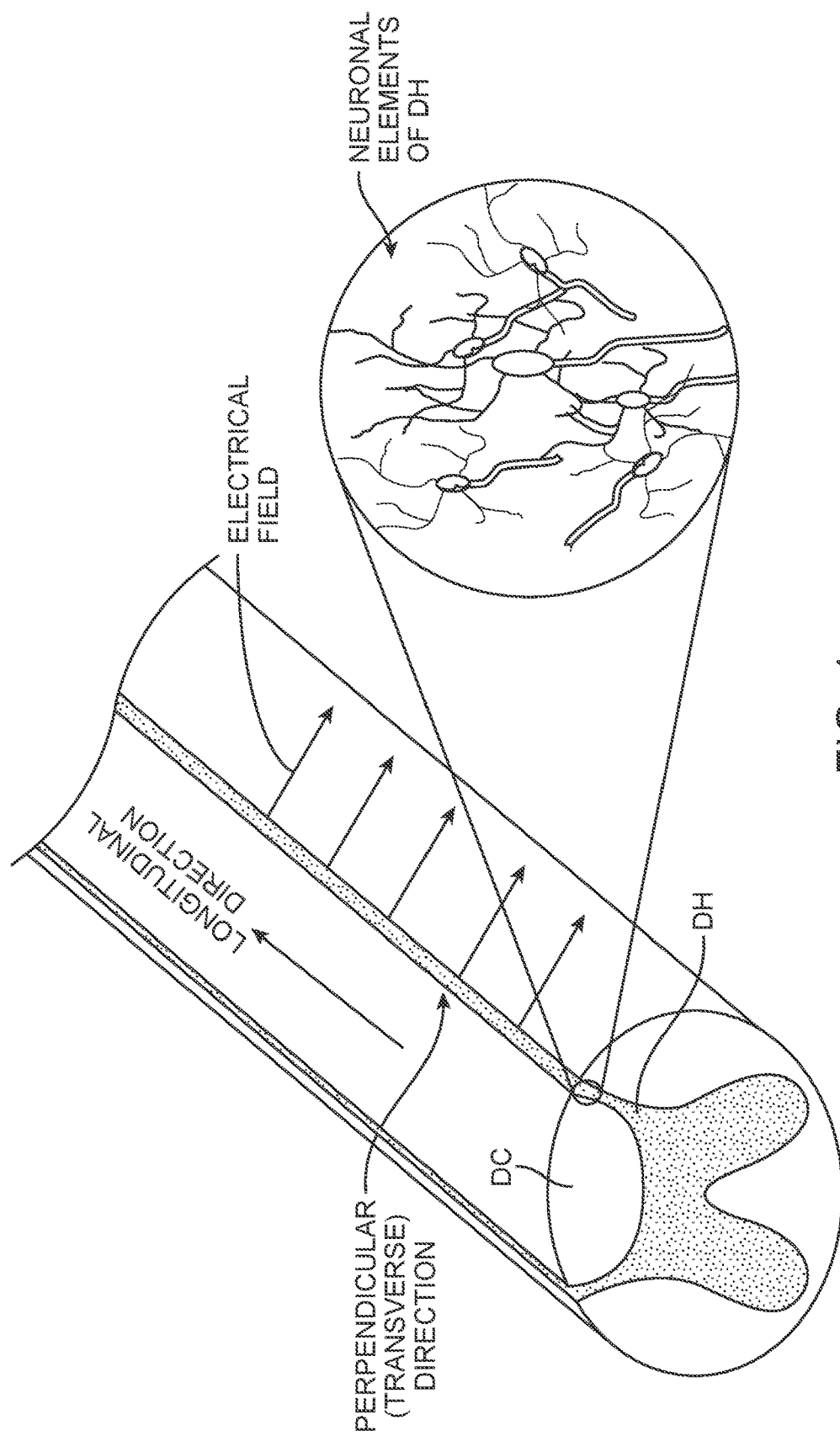
FIG. 1 is a perspective view of a spinal cord, wherein the neuronal elements of the dorsal horn are particularly shown.
Figure 2:
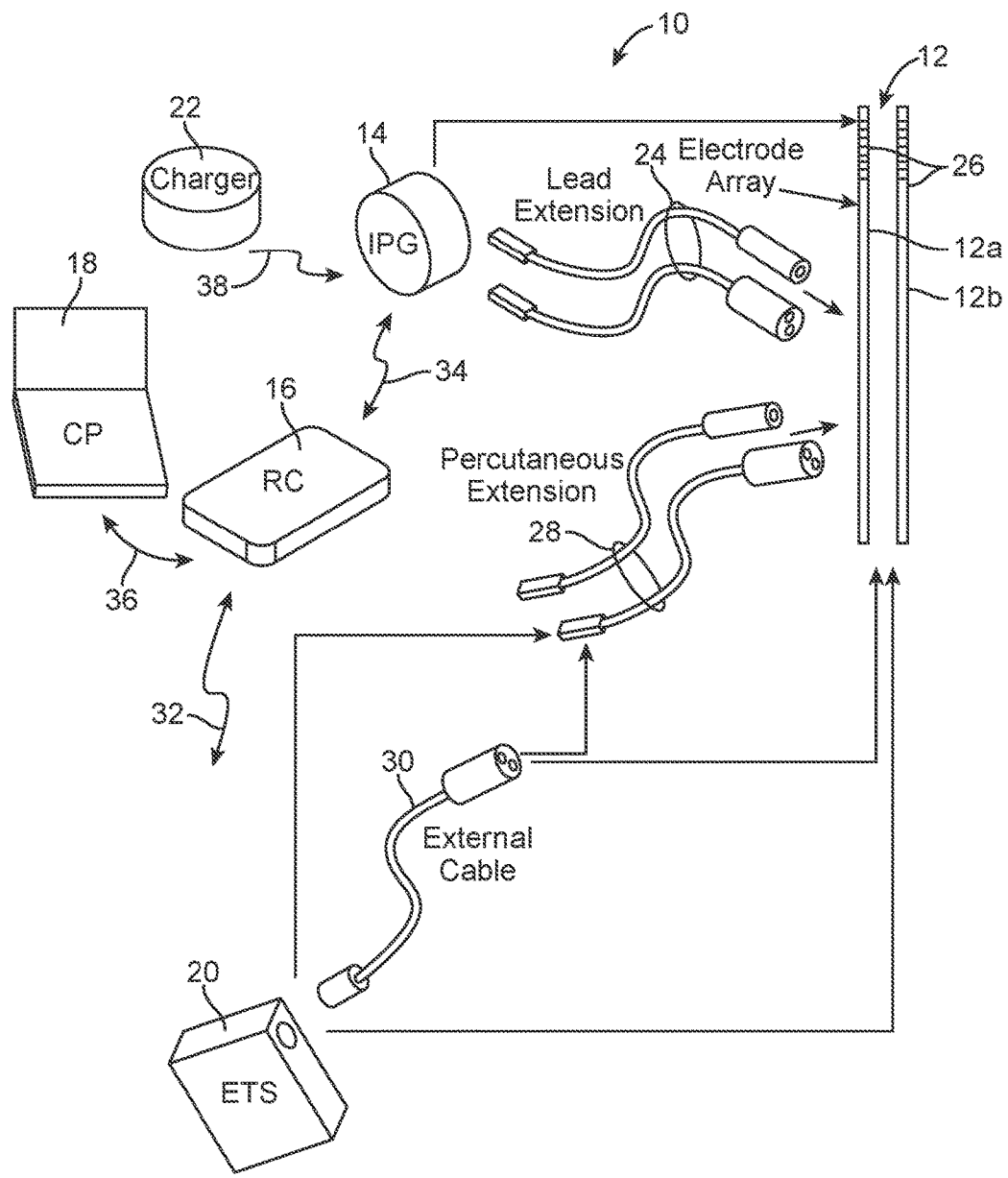
FIG. 2 is plan view of one embodiment of a SCS system arranged in accordance with the present inventions.

Turning first to FIG. 2, an exemplary SCS system 10 constructed in accordance with the present inventions will now be described. The SCS system 10 generally comprises a plurality of neurostimulation leads 12 (in this case, two percutaneous leads 12a and 12b), an implantable pulse generator (IPG) 14, an external remote control (RC) 16, a User's Programmer (CP) 18, an External Trial Stimulator (ETS) 20, and an external charger 22.

The IPG 14 is physically connected via two lead extensions 24 to the neurostimulation leads 12, which carry a plurality of electrodes 26 arranged in an array. In the illustrated embodiment, the neurostimulation leads 12 are percutaneous leads, and to this end, the electrodes 26 are arranged in-line along the neurostimulation leads 12. The number of neurostimulation leads 12 illustrated is two, although any suitable number of neurostimulation leads 12 can be provided, including only one. Alternatively, a surgical paddle lead can be used in place of one or more of the percutaneous leads. As will also be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters. The IPG 14 and neurostimulation leads 12 can be provided as an implantable neurostimulation kit, along with, e.g., a hollow needle, a stylet, a tunneling tool, and a tunneling straw. Further details discussing implantable kits are disclosed in U.S. Application Ser. No. 61/030,506, entitled "Temporary Neurostimulation Lead Identification Device," which is expressly incorporated herein by reference.

The ETS 20 may also be physically connected via percutaneous lead extensions 28 or external cable 30 to the neurostimulation lead 12. The ETS 20, which has similar pulse generation circuitry as the IPG 14, also delivers electrical stimulation energy in the form of a pulsed electrical waveform to the electrode array 26 in accordance with a set of stimulation parameters. The major difference between the ETS 20 and the IPG 14 is that the ETS 20 is a non-implantable device that is used on a trial basis after the neurostimulation lead 12 has been implanted and prior to implantation of the IPG 14, to test the responsiveness of the stimulation that is to be provided. Thus, any functions described herein with respect to the IPG 14 can likewise be performed with respect to the ETS 20.

The RC 16 may be used to telemetrically control the ETS 20 via a bi-directional RF communications link 32. Once the IPG 14 and stimulation leads 12 are implanted, the RC 16 may be used to telemetrically control the IPG 14 via a bi-directional RF communications link 34. Such control allows the IPG 14 to be turned on or off and to be programmed with different stimulation programs after implantation. Once the IPG 14 has been programmed, and its power source has been charged or otherwise replenished, the IPG 14 may function as programmed without the RC 16 being present.

The CP 18 provides user detailed stimulation parameters for programming the IPG 14 and ETS 20 in the operating room and in follow-up sessions. The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown).

The external charger 22 is a portable device used to transcutaneously charge the IPG 14 via an inductive link 38. Once the IPG 14 has been programmed, and its power source has been charged by the external charger 22 or otherwise replenished, the IPG 14 may function as programmed without the RC 16 or CP 18 being present.

For the purposes of this specification, the terms "neurostimulator," "stimulator," "neurostimulation," and "stimulation" generally refer to the delivery of electrical energy that affects the neuronal activity of neural tissue, which may be excitatory or inhibitory; for example by initiating an action potential, inhibiting or blocking the propagation of action potentials, affecting changes in neurotransmitter/neuromodulator release or uptake, and inducing changes in neuroplasticity or neurogenesis of tissue. For purposes of brevity, the details of the RC 16, ETS 20, and external charger 22 will not be described herein. Details of exemplary embodiments of these components are disclosed in U.S. Pat. No. 6,895,280, which is expressly incorporated herein by reference.

Figure 3:
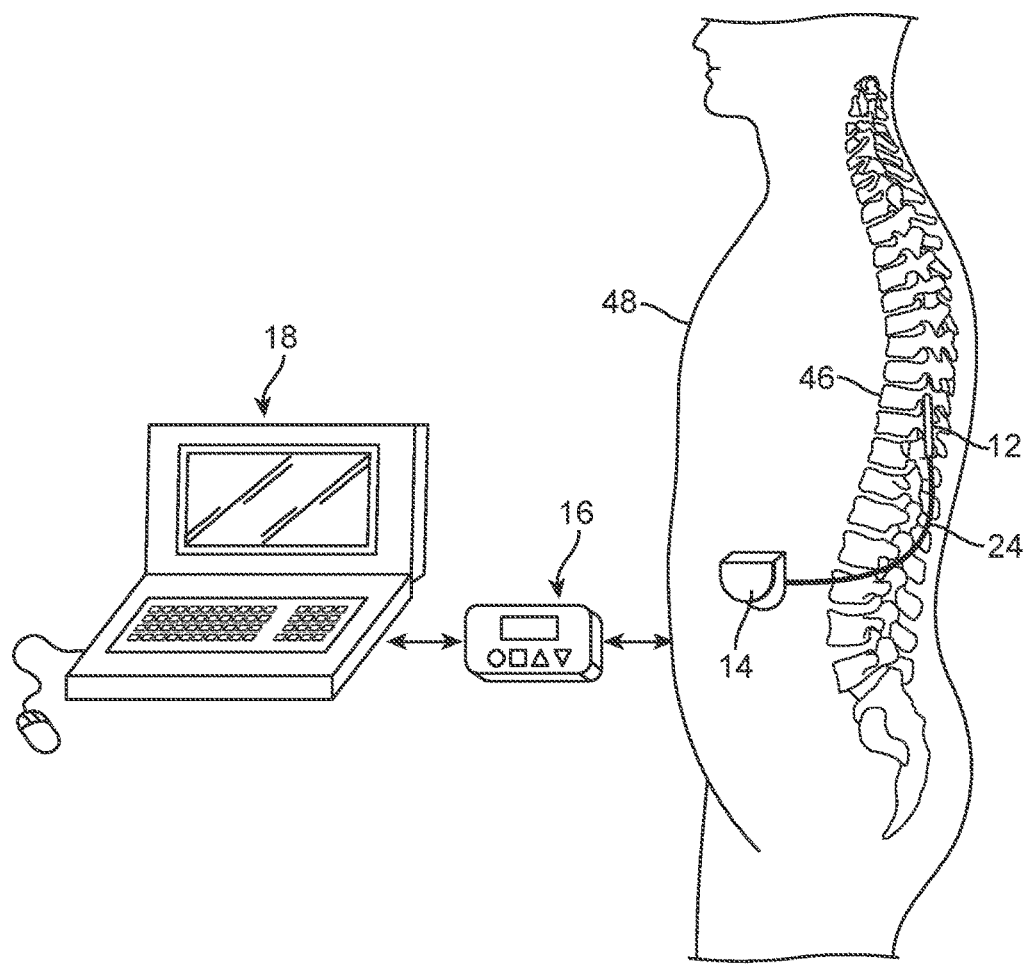
FIG. 3 is a plan view of the SCS system of FIG. 2 in use to perform spinal cord stimulation (SCS) on a patient.

Referring to FIG. 3, the neurostimulation leads 12 are implanted at an initial position within the spinal column 42 of a patient 40. The preferred placement of the neurostimulation leads 12 is adjacent, i.e., resting near, or upon the dura, adjacent to the spinal cord area to be stimulated. In the illustrated embodiment, the neurostimulation leads 12 are implanted along a longitudinal axis of the spinal cord of the patient 40. Due to the lack of space near the location where the neurostimulation leads 12 exit the spinal column 42, the IPG 14 is generally implanted in a surgically-made pocket either in the abdomen or above the buttocks. The IPG 14 may, of course, also be implanted in other locations of the patient's body. The lead extensions 24 facilitate locating the IPG 14 away from the exit point of the neurostimulation leads 12. As there shown, the CP 18 communicates with the IPG 14 via the RC 16. After implantation, the IPG 14 can be operated to generate a volume of activation relative to the target tissue to be treated, thereby providing the therapeutic stimulation under control of the patient.

Figure 4:
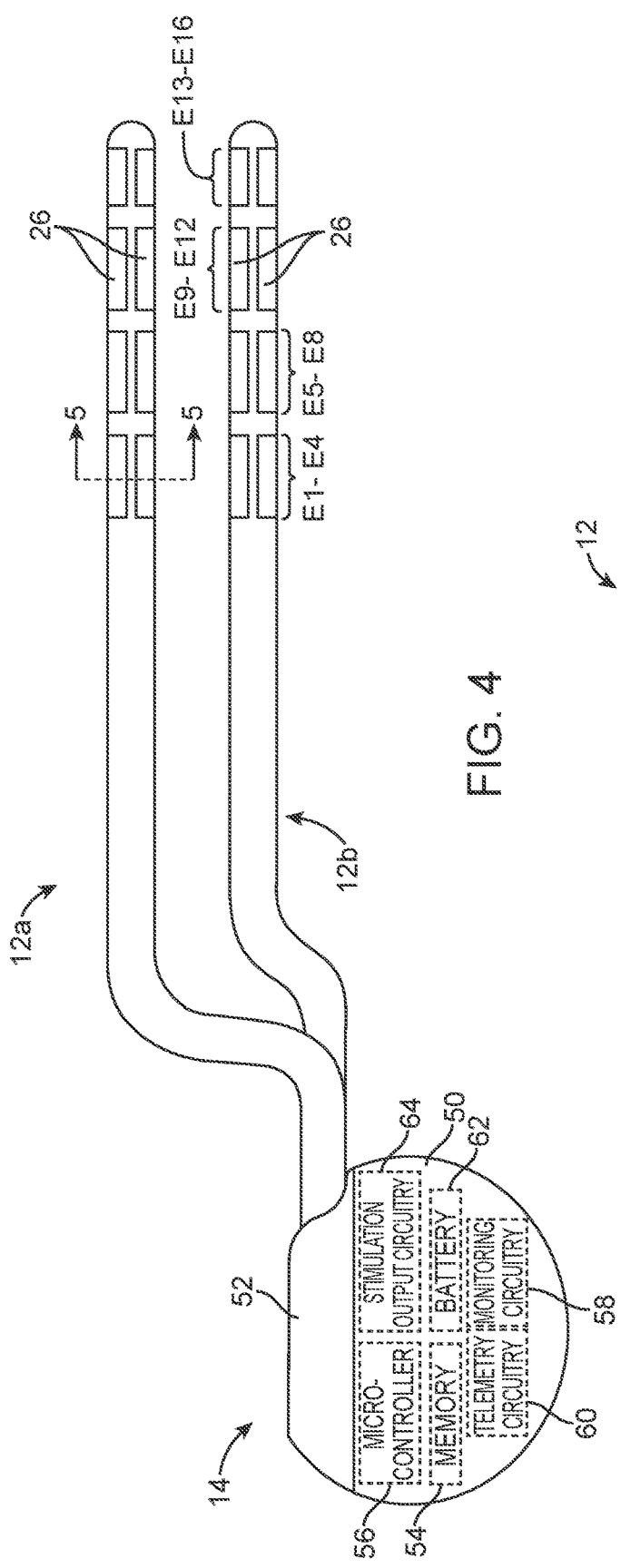
FIG. 4 is a plan view of an implantable pulse generator (IPG) and two neurostimulation leads used in the SCS system of FIG. 1.
Figure 5:
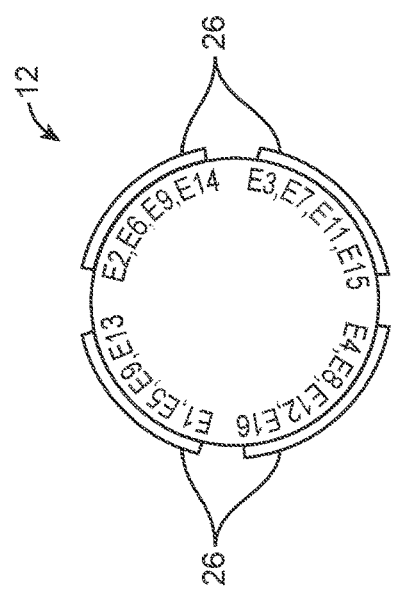
FIG. 5 is a cross-sectional view of one of the neurostimulation leads of FIG. 4, taken along the line 5-5.

Referring now to FIG. 4, the external features of the neurostimulation leads 12a, 12b and the IPG 14 will be briefly described. The electrodes 26 take the form of segmented electrodes that are circumferentially and axially disposed about each of the respective neurostimulation leads 12a, 12b. By way of non-limiting example, and with further reference to FIG. 5, each neurostimulation lead 12 may carry sixteen electrodes, arranged as four rings of electrodes (the first ring consisting of electrodes E1-E4; the second ring consisting of electrodes E5-E8; the third ring consisting of electrodes E9-E12; and the fourth ring consisting of electrodes E13-E16) or four axial columns of electrodes (the first column consisting of electrodes E1, E5, E9, and E13; the second column consisting of electrodes E2, E6, E10, and E14; the third column consisting of electrodes E3, E7, E11, and E15; and the fourth column consisting of electrodes E4, E8, E12, and E16). The actual number and shape of leads and electrodes will, of course, vary according to the intended application. Further details describing the construction and method of manufacturing percutaneous stimulation leads are disclosed in U.S. patent application Ser. No. 11/689,918, entitled "Lead Assembly and Method of Making Same," and U.S. patent application Ser. No. 11/565,547, entitled "Cylindrical Multi-Contact Electrode Lead for Neural Stimulation and Method of Making Same," the disclosures of which are expressly incorporated herein by reference.

The IPG 14 comprises an outer case 50 for housing the electronic and other components (described in further detail below). The outer case 50 is composed of an electrically conductive, biocompatible material, such as titanium, and forms a hermetically sealed compartment wherein the internal electronics are protected from the body tissue and fluids. In some cases, the outer case 50 may serve as an electrode. The IPG 14 further comprises a connector 52 to which the proximal ends of the neurostimulation leads 12 mate in a manner that electrically couples the electrodes 26 to the internal electronics (described in further detail below) within the outer case 50. To this end, the connector 52 includes two ports (not shown) for receiving the proximal ends of the leads 12. In the case where the lead extensions 24 are used, the ports may instead receive the proximal ends of such lead extensions 24.

As briefly discussed above, the IPG 14 includes circuitry that provides electrical stimulation energy to the electrodes 26 in accordance with a set of parameters. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), pulse rate (measured in pulses per second), and burst rate (measured as the stimulation on duration X and stimulation off duration Y). As will be described in further detail below, the IPG 14 also includes circuitry that provides electrical signals, and measured electrical impedance in response to the electrical signals.

With respect to the pulsed electrical waveform provided during operation of the SCS system 10, electrodes that are selected to transmit or receive electrical energy are referred to herein as "activated," while electrodes that are not selected to transmit or receive electrical energy are referred to herein as "non-activated." Electrical energy delivery will occur between two (or more) electrodes, one of which may be the IPG case 50, so that the electrical current has a path from the energy source contained within the IPG case 50 to the tissue and a sink path from the tissue to the energy source contained within the case. Electrical energy may be transmitted to the tissue in a monopolar or multipolar (e.g., bipolar, tripolar, etc.) fashion.

Monopolar delivery occurs when a selected one or more of the lead electrodes 26 is activated along with the case 50 of the IPG 14, so that electrical energy is transmitted between the selected electrode 26 and case 50. Monopolar delivery may also occur when one or more of the lead electrodes 26 are activated along with a large group of lead electrodes located remotely from the one or more lead electrodes 26 so as to create a monopolar effect; that is, electrical energy is delivered from the one or more lead electrodes 26 in a relatively isotropic manner. Bipolar delivery occurs when two of the lead electrodes 26 are activated as anode and cathode, so that electrical energy is transmitted between the selected electrodes 26. Tripolar delivery occurs when three of the lead electrodes 26 are activated, two as anodes and the remaining one as a cathode, or two as cathodes and the remaining one as an anode.

The IPG 14 comprises electronic components, such as a memory 54, controller/processor (e.g., a microcontroller) 56, monitoring circuitry 58, telemetry circuitry 60, a battery 62, stimulation output circuitry 64, and other suitable components known to those skilled in the art.

The memory 54 is configured for storing programming packages, stimulation parameters, measured physiological information, and other important information necessary for proper functioning of the IPG 14. The microcontroller 56 executes a suitable program stored in memory 54 for directing and controlling the neurostimulation performed by IPG 14. The monitoring circuitry 58 is configured for monitoring the status of various nodes or other points throughout the IPG 14, e.g., power supply voltages, temperature, battery voltage, and the like. Notably, the electrodes 26 fit snugly within the patient, and because the tissue is conductive, electrical measurements can be taken between the electrodes 26. Thus, the monitoring circuitry 58 is configured for taking such electrical measurements (e.g., electrode impedance, field potential, evoked action potentials, etc.) for performing such functions as detecting fault conditions between the electrodes 26 and the stimulation output circuitry 64, determining the coupling efficiency between the electrodes 26 and the tissue, determining the posture/patient activity of the patient, facilitating lead migration detection.

More significant to the present inventions, an evoked potential measurement technique can be used to calibrate the stimulation energy delivered to the spinal cord. The evoked potential measurement technique may be performed by generating an electrical field at one of the electrodes 26, which is strong enough to depolarize the neurons adjacent the stimulating electrode beyond a threshold level, thereby inducing the firing of action potentials (APs) that propagate along the neural fibers. Such stimulation is preferably suprathreshold, but not uncomfortable. A suitable stimulation pulse for this purpose is, for example, 4 mA for 200 μs. While a selected one of the electrodes 26 is activated to generate the electrical field, a selected one or ones of the electrodes 26 (different from the activated electrode) is operated to record a measurable deviation in the voltage caused by the evoked potential due to the stimulation pulse at the stimulating electrode.

The telemetry circuitry 60, including an antenna (not shown), is configured for receiving programming data (e.g., the operating program and/or stimulation parameters, including pulse patterns) from the RC 16 and/or CP 18 in an appropriate modulated carrier signal, which the programming data is then stored in the memory 54. The telemetry circuitry 60 is also configured for transmitting status data to the RC 16 and/or CP 18 in an appropriate modulated carrier signal. The battery 62, which may be a rechargeable lithium-ion or lithium-ion polymer battery, provides operating power to IPG 14. The stimulation output circuitry 64 is configured for, under control of the microcontroller 56, generating and delivering electrical energy, in the form of electrical pulse trains, to each of the electrodes 26, as well as any electrical signals needed for acquiring electrical measurements.

Notably, while the microcontroller 56 is shown in FIG. 4 as a single device, the processing functions and controlling functions can be performed by a separate controller and processor. Thus, it can be appreciated that the controlling functions performed by the IPG 14 can be performed by a controller, and the processing functions performed by the IPG 14 can be performed by a processor. Additional details concerning the above-described and other IPGs may be found in U.S. Pat. No. 6,516,227, U.S. Patent Publication No. 2003/0139781, and U.S. patent application Ser. No. 11/138,632, entitled "Low Power Loss Current Digital-to-Analog Converter Used in an Implantable Pulse Generator," which are expressly incorporated herein by reference. It should be noted that rather than an IPG, the SCS system 10 may alternatively utilize an implantable receiver-modulator (not shown) connected to the leads 12. In this case, the power source, e.g., a battery, for powering the implanted receiver, as well as control circuitry to command the receiver-modulator, will be contained in an external controller inductively coupled to the receiver-modulator via an electromagnetic link. Data/power signals are transcutaneously coupled from a cable-connected transmission coil placed over the implanted receiver-modulator. The implanted receiver-modulator receives the signal and generates the stimulation in accordance with the control signals.

More significant to the present inventions, the SCS system 10 delivers electrical stimulation energy to the spinal cord of the patient in accordance with a stimulation program that preferentially stimulates dorsal horn neuronal elements over dorsal column neuronal elements in the spinal cord.

To this end, the current delivered from the electrodes 26 is fractionalized, such that the electrical field generated by the neurostimulation lead(s) 12 has an electrical field strength in the longitudinal direction that is approximately equal, resulting in a voltage gradient of approximately zero along the dorsal column. This substantially constant electrical field forms a small longitudinal gradient, which minimizes activation of the large myelinated axons in the dorsal column. In contrast, the electrical field generated by the neurostimulation lead(s) 12 has an electrical field strength in the transverse direction that substantially differs, resulting a strong voltage gradient in the dorsal horn. In particular, the transverse electrical field strength is greatest adjacent the neurostimulation lead(s) 12 and falls off laterally, resulting in a sizable gradient in the transverse direction, which activates the neural cell terminals in the dorsal horn. Thus, the substantially constant longitudinal electrical field and the large gradient in the transverse electrical field favor stimulation of dorsal horn neuronal elements over dorsal column neuronal elements. This electrical field makes the dorsal column neuronal elements even less excitable relative to the dorsal horn neuronal elements. In this manner, the perception of paresthesia is eliminated or at least minimized. In the illustrated embodiment, the all of the electrodes 26 on the neurostimulation leads 12 are preferably activated to maximize the stimulation of the dorsal horn neuronal elements along the leads 12.

Calibration techniques (described below) may be used to determine the proper current fractionalization for the electrodes 26. With the current fractionalized to a plurality of electrodes 26 on the neurostimulation lead 12, the resulting field can be calculated by superimposing the fields generated by the current delivered to each electrode 26. In the illustrated embodiment, the electrodes 26 on the neurostimulation lead 12(*s*) are anodic, while the outer case 44 of the IPG 14 is cathodic. In this manner, a monopolar anodic electrical field is generated by the SCS system 10. Further details discussing techniques for preferentially stimulating dorsal horn neuronal elements over dorsal column neuronal elements are described in U.S. Provisional Patent Application Ser. No. 61/911,728, entitled "Systems and Methods for Delivering Therapy to the Dorsal Horn of a Patient," which is expressly incorporated herein by reference.

Significantly, the SCS system 10 delivers the electrical energy to the spinal cord of the patient by generating a plurality of electrical fields having different orientations that target the different directions/orientations of the dorsal horn neuronal elements, as illustrated in FIG. 6. In this manner, all, or at least a significant amount of, the dorsal horn neuronal elements will be stimulated by at least one of the electrical fields.

Figure 7A:
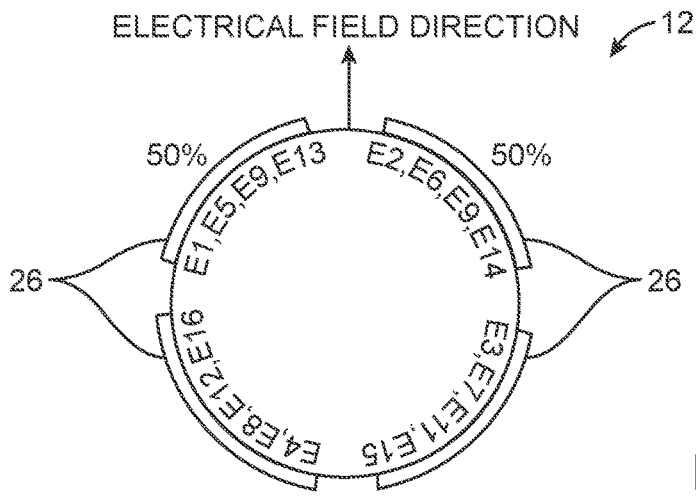
FIGS. 7a-7c are plan views of one of the neurostimulation leads of FIG. 4, particularly showing the generation of electrical fields at different medio-lateral directions.
Figure 7B:
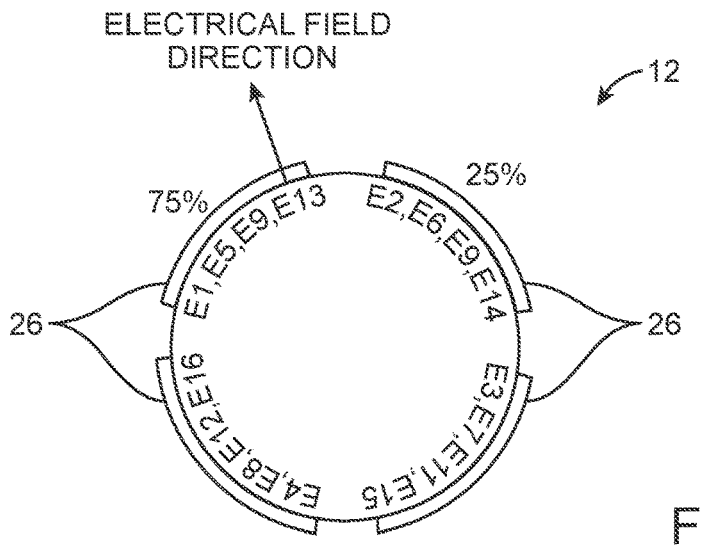
Figure 7C:
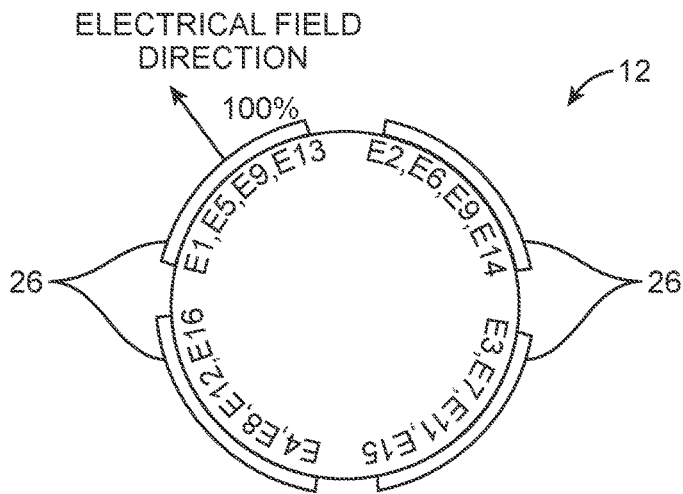

In the illustrated embodiment, the electrical fields are oriented in different medio-lateral directions (i.e., the direction of the electrical fields as projected on a transverse plane through the spinal cord). To generate electrical fields in different medio-lateral directions, the electrodes 26 may have different current fractionalizations in the radial direction. For example, referring back to FIG. 5, the first column of electrodes E1, E5, E9, and E13 may deliver 50% of the anodic current, and the second column of electrodes E2, E6, E10, and E14 may deliver the remaining 50% of the anodic current to orient the electrical field in one medio-lateral direction, as illustrated in FIG. 7a. The first column of electrodes E1, E5, E9, and E13 may deliver 75% of the anodic current, and the second column of electrodes E2, E6, E10, and E14 may deliver the remaining 25% of the anodic current to orient the electrical field in one medio-lateral direction to orient the electrical field in another medio-lateral direction, as illustrated in FIG. 7b. The first column of electrodes E1, E5, E9, and E13 may deliver 100% of the anodic current to orient the electrical field in one medio-lateral direction to orient the electrical field in another medio-lateral direction, as illustrated in FIG. 7c.

Figure 8A:
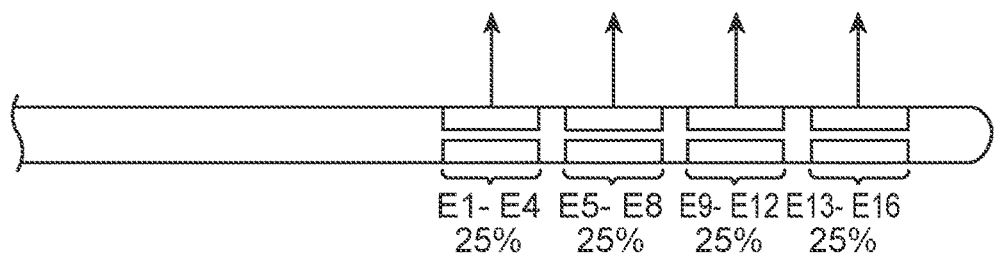
FIGS. 8a-8c are plan views of one of the neurostimulation leads of FIG. 4, particularly showing the generation of electrical fields at different rostro-caudal directions.
Figure 8B:
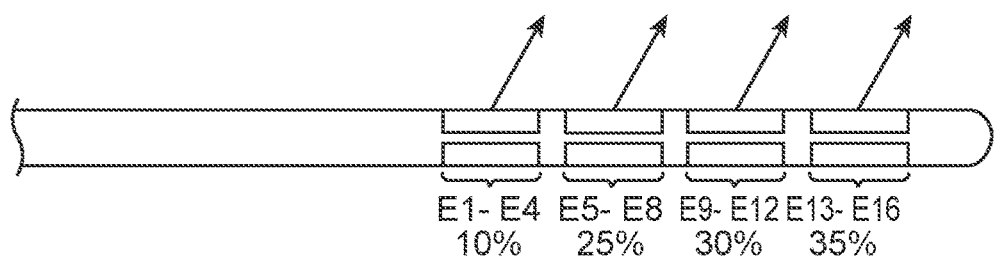
Figure 8C:
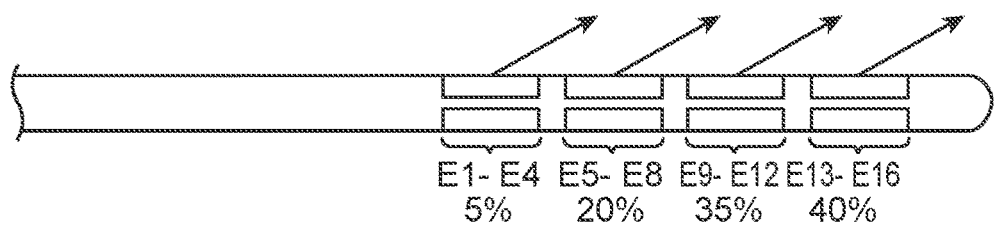

Although it is desirable that the electrical fields preferentially stimulate dorsal horn neuronal elements over the dorsal column neuronal elements, as discussed above, the electrical fields may still be oriented in different rostro-caudal directions (i.e., the direction of the electrical fields as projected on a longitudinal plane through the spinal cord), although preferably not in an orientation that will result in the perception of paresthesia. To generate electrical fields in different rostro-caudal directions, the electrodes 26 may have different current fractionalizations in the longitudinal direction. For example, referring back to FIG. 5, each of the first ring of electrodes E1-E4, the second ring of electrodes E5-E8; the third ring of electrodes E9-E12, and the fourth ring of electrodes E13-E16 may deliver 25% of the anodic current to orient the electrical field in one rostro-caudal direction, as illustrated in FIG. 8a. The first ring of electrodes E1-E4, may deliver 10% of the anodic current, the second ring of electrodes E5-E8 may deliver 25% of the anodic current, the third ring of electrodes E9-E12 may deliver 30% of the anodic current, and the fourth ring of electrodes E13-E16 may deliver 35% of the anodic current to orient the electrical field in one rostro-caudal direction, as illustrated in FIG. 8b. The first ring of electrodes E1-E4, may deliver 5% of the anodic current, the second ring of electrodes E5-E8 may deliver 20% of the anodic current, the third ring of electrodes E9-E12 may deliver 35% of the anodic current, and the fourth ring of electrodes E13-E16 may deliver 40% of the anodic current to orient the electrical field in one rostro-caudal direction, as illustrated in FIG. 8c.

Figure 9:
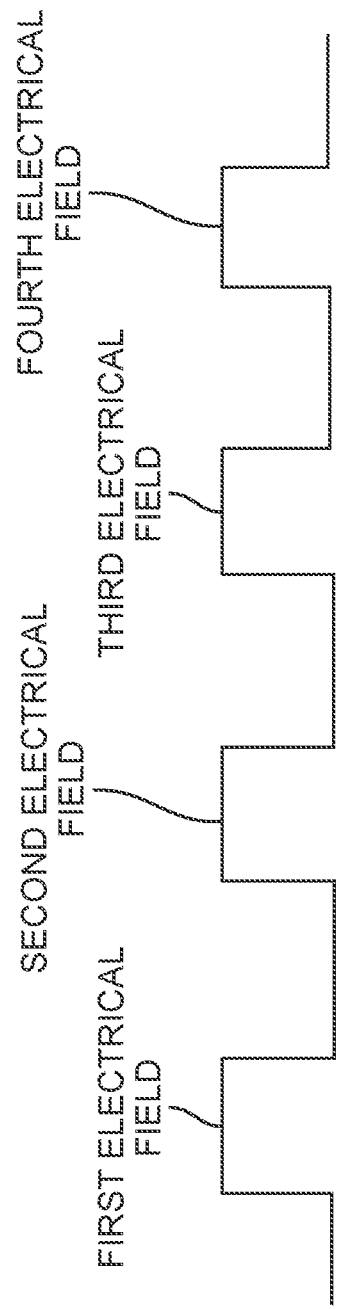
FIG. 9 is a timing diagram of a pulse pattern having electrical fields that are generated on a pulse-by-pulse basis using the SCS system of FIG. 2.

The different electrical fields generated by the SCS system 10 preferably achieve a temporal summation of stimulation in the dorsal horn neuronal elements. To ensure this temporal summation of stimulation, the electrical fields can be generated respectively on a pulse-by-pulse basis. For example, as illustrated in FIG. 9, a first electrical field can be generated by the electrodes 26 (using a first current fractionalization) during a first electrical pulse of the pulsed waveform, a second different electrical field can be generated by the electrodes 26 (using a second different current fractionalization) during a second electrical pulse of the pulsed waveform, a third different electrical field can be generated by the electrodes 26 (using a third different current fractionalization) during a third electrical pulse of the pulsed waveform, a fourth different electrical field can be generated by the electrodes 26 (using a fourth different current fractionalized) during a fourth electrical pulse of the pulsed waveform, and so forth. Further details on the delivery of different electrical fields on a pulse-by-pulse basis are set forth in U.S. Provisional Patent Application Ser. No. 62/020, 836, which is expressly incorporated herein by reference.

The electrical fields generated by the SCS system 10 may be rotated or cycled through multiple times under a timing scheme. The electrical field cycling can be accomplished in any one of a variety of manners. In one embodiment, the different electrical fields are generated in the same (or regular) order during the electrical field cycles. For example, if four electrical fields labeled 1-4 are generated, the order in which these electrical fields are generated may be {2, 3, 1, 4}, {2, 3, 1, 4}, {2, 3, 1, 4}, etc. The different electrical field may alternatively be generated in a different order (or irregular) during the electrical field cycles. For example, the order in which electrical fields 1-4 are generated may be {1, 2, 3, 4}, {3, 1, 2, 4}, {4, 1, 3, 21, 11, 2, 3, 4}, etc.

Although electrical fields 1-4 have been described as being generated the same number of times for each electrical field cycle (in the cases above, one time per each cycle), the electrical fields 1-4 may be generated a different number of times for each electrical field cycle. That is, the cycling can be biased towards one electrical field relative to another electrical field. For example, electrical fields 1-4 may be generated during the electrical field cycles as follows: {1, 2, 2, 2, 3, 3, 4}, {1, 2, 2, 2, 3, 3, 4}, {1, 2, 2, 2, 3, 3, 4}, etc. Thus, in this case, electrical field 1 is generated once, electrical field 2 is generated thrice, electrical field 3 is generated twice, and electrical field 4 is generated once per electrical field cycle.

In the above exemplary cases, the electrical fields 1-4 can be generated at a continuous pulse rate. However, in an optional embodiment, the electrical field cycles can be bursted on and off. For example, an electrical field cycle {2, 3, 1, 4} can be repeatedly bursted at a defined frequency (e.g., a cycle burst every 100 ms). In one particularly useful embodiment, the burst frequency matches the pathological burst frequency of the neurological signals that cause the chronic pain.

Although the interpulse interval (i.e., the time between adjacent pulses), pulse amplitude, and pulse duration during the electrical field cycles has been described as being uniform, the interpulse interval, pulse amplitude, and/or pulse duration may vary within the electrical field cycle, as described in U.S. Provisional Patent Application Ser. No. 62/020,836, which has previously been incorporated herein by reference.

Because the stimulation threshold (i.e., the electrical current needed on an activated electrode to stimulate adjacent tissue) varies from patient to patient and from electrode 26 to electrode 26 within a patient, a more accurate fractionalization of the current between electrodes 26 to generate the various electrical fields requires modification of the fractionalization based on the stimulation threshold at each electrode. To this end, the electrodes may be calibrated by determining the stimulation threshold level (i.e., the electrical current needed on an activated electrode to stimulate adjacent tissue) for each of the electrodes and using the stimulation threshold levels to determine the fractionalized electrical current values for generating the electrical fields. This calibration technique may involve calculating a driving force directed to each electrode.

Preferably, the stimulation threshold for each of the electrodes 26 is determined by automatically delivering electrical energy from each of the electrodes 26 at different amplitudes, automatically measuring an evoked compound action potential in response to the deliverance of the electrical energy from each of the electrodes 26, and automatically recording the amplitude at which the evoked compound action potential is measured for each of the electrodes 26. The electrical energy may be delivered to each electrode in a monopolar mode as either anodic or cathodic electrical energy. This automated electrode calibration technique can be updated periodically or in response to a particular event, such as a posture change of the patient.

Determination of the stimulation thresholds may be binary in nature, meaning that the presence or absence of a measured evoked compound action potential either indicates that a stimulation threshold has been reached or not reached for a particular electrode, or the determination of the stimulation thresholds may be more sophisticated in nature. The maximum amplitude of the electrical energy delivered from each electrode should be managed so that the patient does not perceive the electrical stimulation too much, although since single electrical pulses can be used, the patient may not perceive much even at amplitudes that would be strong enough to cause continuous stimulation.

Optionally, the stimulation threshold determined previous electrodes, including the first calibrated electrode, may be used as a starting point for the stimulation threshold determination for subsequent electrodes, so that the amplitude need not be initially set to zero for each subsequently electrode in order to speed up the calibration process. For example, the electrical energy may be transitioned between electrodes at an amplitude where the patient barely perceives stimulation, a comfortable level, or some other constant level.

Alternatively, the stimulation threshold for each of the electrodes 26 may be determined by automatically delivering electrical energy from each of the electrodes 26 at different amplitudes, acquiring feedback from the patient, and in particular communicating when the patient perceives paresthesia, in response to the deliverance of the electrical energy from each of the electrodes 26, and automatically recording the amplitude at which paresthesia is perceived by the patient for each of the electrodes 26. However, it should be appreciated that measuring evoked compound action potentials, as opposed to relying on subjective patient feedback, is objective in nature, can be performed quickly, and can be determined using a relatively small number of electrical pulses as opposed perceiving paresthesia, which requires a relatively large number of electrical pulses.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A non-transitory machine-readable medium including instructions, which when executed by a neuromodulator connected to implanted electrodes which are operably positioned near a spinal cord, cause the neuromodulator to provide a therapy using implanted electrodes to a patient having a medical condition, including deliver electrical energy as a pulsed electrical waveform to the targeted neuronal elements in accordance with a stimulation program that preferentially stimulates the targeted neuronal elements, wherein the pulsed electrical waveform to the targeted neuronal elements produces a first electrical field to the targeted neuronal elements where the first electrical field has a first orientation during at least a first pulse in the pulsed electrical waveform, a second electrical field to the targeted neuronal elements where the second electrical field has a second orientation during at least a second pulse in the pulsed electrical waveform, and a third electrical field to the targeted neuronal elements where the third electrical field has a third orientation during at least a third pulse in the pulsed electrical waveform the first, second and third orientations being different from each other.

2. The non-transitory machine-readable medium of claim 1, wherein the pulsed electrical waveform includes repeating electrical field cycles, wherein each of the repeating electrical field cycles includes the first electrical field, the second electrical field, and the third electrical field.

3. The non-transitory machine-readable medium of claim 2, wherein each of the first electrical field, the second electrical field and the third electrical field within each of the repeating electrical field cycles includes a same number of pulses.

4. The non-transitory machine-readable medium of claim 2, wherein each of the first electrical field, the second electrical field and the third electrical field within each of the repeating electrical field cycles includes a different number of pulses.

5. The non-transitory machine-readable medium of claim 2, wherein the electrical fields are generated in a same order during the electrical field cycles.

6. The non-transitory machine-readable medium of claim 2, wherein the electrical fields are generated in a different order during the electrical field cycles.

7. The non-transitory machine-readable medium of claim 2, wherein the repeating electrical field cycles are bursted on and off at a burst frequency.

8. The non-transitory machine-readable medium of claim 2, wherein the electrical field cycles include a bias toward one of the first, second or third electrical fields relative to the other ones of the first, second or third electrical fields.

9. The non-transitory machine-readable medium of claim 1, wherein the first, second and third electrical fields are rotated through under a timing scheme.

10. A system for providing a therapy to a patient using electrodes which are implanted operably near a spinal cord, the system comprising a neuromodulator including stimulation output circuitry and a controller/processor, wherein:
    the stimulation output circuitry is configured to be electrically connected to the electrodes; and
    the controller/processor is configured to cooperate with the stimulation output circuitry to provide the therapy to the patient by delivering electrical stimulation energy as a pulsed electrical waveform using the electrodes in accordance with a stimulation program that preferentially stimulates targeted neuronal elements, wherein the controller/processor is configured to cooperate with the stimulation output circuitry to generate a first electrical field to the targeted neuronal elements where the first field has a first orientation during at least a first pulse in the pulsed electrical waveform, a second electrical field to the targeted neuronal elements where the second field has a second orientation during at least a second pulse in the pulsed electrical waveform, and a third electrical field to the targeted neuronal elements where the third field has a third orientation during at least a third pulse in the pulsed electrical waveform, the first, second and third orientations being different from each other.

11. The system of claim 10, wherein the controller/processor is configured to cooperate with the stimulation output circuitry to provide an electrical field with a longitudinal voltage gradient along the spinal cord that is smaller than a voltage gradient in a transverse direction.

12. The system of claim 10, wherein the first, second and third orientations comprise different medio-lateral directions.

13. The system of claim 10, wherein the controller/processor is configured to cooperate with the stimulation output circuitry to generate the first electrical field using a first current fractionalization, the second electrical field using a second current fractionalization, and the third electrical field using a third current fractionalization, wherein the first, second, and third current fractionalizations are different from each other.

14. A method implemented using a neuromodulator connected to implanted electrodes which are operably positioned near a spinal cord, the method comprising:
using the neuromodulator to provide a therapy to targeted neuronal elements, including using the implanted electrodes to deliver the electrical energy as a pulsed electrical waveform to the targeted neuronal elements in accordance with a stimulation program that preferentially stimulates the targeted neuronal elements, wherein the pulsed electrical waveform provides a first electrical field to the targeted neuronal elements where the first electric field has a first orientation during at least a first pulse in the pulsed electrical waveform, a second electrical field to the targeted neuronal elements where the second electric field has a second orientation during at least a second pulse in the pulsed electrical waveform, and a third electrical field to the targeted neuronal elements where the third electric field has a third orientation during at least a third pulse in the pulsed electrical waveform, and wherein the first, second and third orientations are different from each other.

15. The method of claim 14, further comprising using a first current fractionalization to generate the first electrical field, using a second current fractionalization to generate the second electrical field, and using a third current fractionalization to generate the third electrical field.

16. The method of claim 14, wherein the first, second and third orientations comprise different medio-lateral directions.

17. The method of claim 14, wherein the pulsed electrical waveform produces a longitudinal voltage gradient along the spinal cord that is smaller than a voltage gradient in a transverse direction.

18. The method of claim 14, wherein the first electrical field is generated using a first current fractionalization, the second electrical field is generated using a second current fractionalization, and the third electrical field is generated using a third current fractionalization, wherein the first, second, and third current fractionalizations are different from each other.

19. The method of claim 14, wherein the pulsed electrical waveform includes repeating electrical field cycles, wherein the electrical fields are generated in a same order during the electrical field cycle, and each of the repeating electrical field cycles includes the first electrical field, the second electrical field, and the third electrical field.

20. The method of claim 14, wherein the pulsed electrical waveform includes repeating electrical field cycles, wherein the electrical fields are generated in a different order during the electrical field cycles, and each of the repeating electrical field cycles includes the first electrical field, the second electrical field, and the third electrical field.

* * * * *